United States Patent
Seymour

(10) Patent No.: US 10,245,062 B2
(45) Date of Patent: Apr. 2, 2019

(54) SURGICAL GUIDE

(71) Applicant: Segway Orthopaedics, Inc., Carlsbad, CA (US)

(72) Inventor: Stuart Seymour, Carlsbad, CA (US)

( * ) Notice: Subject to any disclaimer, the term of this patent is extended or adjusted under 35 U.S.C. 154(b) by 42 days.

(21) Appl. No.: 15/106,500

(22) PCT Filed: Nov. 26, 2014

(86) PCT No.: PCT/US2014/067670
§ 371 (c)(1),
(2) Date: Jun. 20, 2016

(87) PCT Pub. No.: WO2015/081231
PCT Pub. Date: Jun. 4, 2015

(65) Prior Publication Data
US 2016/0345998 A1    Dec. 1, 2016

(51) Int. Cl.
*A61B 17/32* (2006.01)
*A61B 17/17* (2006.01)
*A61B 1/00* (2006.01)
*A61B 17/16* (2006.01)
*A61B 90/30* (2016.01)
*A61B 90/00* (2016.01)

(52) U.S. Cl.
CPC ...... *A61B 17/320016* (2013.01); *A61B 17/17* (2013.01); *A61B 17/320036* (2013.01); *A61B 1/00165* (2013.01); *A61B 17/1604* (2013.01); *A61B 2017/320052* (2013.01); *A61B 2090/306* (2016.02); *A61B 2090/3614* (2016.02)

(58) Field of Classification Search
CPC .. A61B 2017/004; A61B 2017/320052; A61B 2017/320056; A61B 2017/32113; A61B 17/320016; A61B 17/320036; A61B 17/17; A61B 17/3211; A61B 17/3423; A61M 25/065; A61M 25/0662
See application file for complete search history.

(56) References Cited

U.S. PATENT DOCUMENTS

| | | | | |
|---|---|---|---|---|
| 6,179,852 B1* | 1/2001 | Strickland | ...... | A61B 17/320036 606/167 |
| 8,252,011 B1* | 8/2012 | Forrester | ........ | A61B 17/320016 606/167 |
| 8,771,303 B1* | 7/2014 | Jurbala | .......... | A61B 17/320036 606/170 |
| 2003/0028147 A1* | 2/2003 | Ayes | .................. | A61B 17/3401 604/164.06 |
| 2004/0054378 A1* | 3/2004 | Yang | .............. | A61B 17/320036 606/191 |
| 2004/0267243 A1* | 12/2004 | Klotz | ............. | A61B 17/320036 606/1 |

(Continued)

*Primary Examiner* — Eric Rosen
*Assistant Examiner* — Chima Igboko
(74) *Attorney, Agent, or Firm* — Donn K. Harms

(57) ABSTRACT

A surgical device is provided which is formed of a pair of engageable members each having first and second channels which define respective first and second tunnels through the removably engaged members. Apertures through a proximal endwall provide a path for a cabled imaging component through said first tunnel to provide images of tissue surrounding the device, and an opening in the endwall of the paired members provides access to the second tunnel for a surgical blade for cutting tissue positioned in a gap between the paired members.

3 Claims, 3 Drawing Sheets

(56) References Cited

U.S. PATENT DOCUMENTS

| | | | | |
|---|---|---|---|---|
| 2005/0021048 A1* | 1/2005 | Kuhlman | A61M 25/065 | 606/108 |
| 2005/0096645 A1* | 5/2005 | Wellman | A61B 17/320016 | 606/41 |
| 2006/0276782 A1* | 12/2006 | Gedebou | A61B 17/320036 | 606/45 |
| 2007/0288043 A1* | 12/2007 | Rehnke | A61B 1/313 | 606/170 |
| 2009/0048620 A1* | 2/2009 | Weiss | A61B 17/320036 | 606/167 |
| 2011/0087258 A1* | 4/2011 | Sluss | A61B 17/320036 | 606/170 |
| 2012/0016397 A1* | 1/2012 | Briganti | A61B 17/320036 | 606/167 |
| 2014/0052166 A1* | 2/2014 | Haindl | A61B 17/3421 | 606/185 |
| 2014/0088518 A1* | 3/2014 | Knapp | A61B 1/307 | 604/284 |
| 2014/0094798 A1* | 4/2014 | Garrison | A61B 18/1445 | 606/42 |
| 2014/0097227 A1* | 4/2014 | Aronhalt | A61B 17/0682 | 227/180.1 |
| 2014/0336581 A1* | 11/2014 | Collin | A61B 25/0668 | 604/164.05 |
| 2015/0034695 A1* | 2/2015 | Kapadia | A61B 17/07207 | 227/175.4 |
| 2015/0306352 A1* | 10/2015 | Banerian | A61M 25/0662 | 604/544 |
| 2016/0015447 A1* | 1/2016 | Rosa | A61B 18/1445 | 606/130 |
| 2016/0058437 A1* | 3/2016 | Penna | A61B 17/0467 | 606/145 |
| 2016/0128714 A1* | 5/2016 | DaSilva | A61B 17/320036 | 606/170 |
| 2016/0157881 A1* | 6/2016 | Seymour | A61B 17/3211 | 606/172 |
| 2017/0173306 A1* | 6/2017 | Kumar | A61M 25/0662 | |
| 2017/0348467 A1* | 12/2017 | Park | A61M 1/00 | |
| 2018/0008302 A9* | 1/2018 | Seymour | A61B 17/3211 | |

* cited by examiner

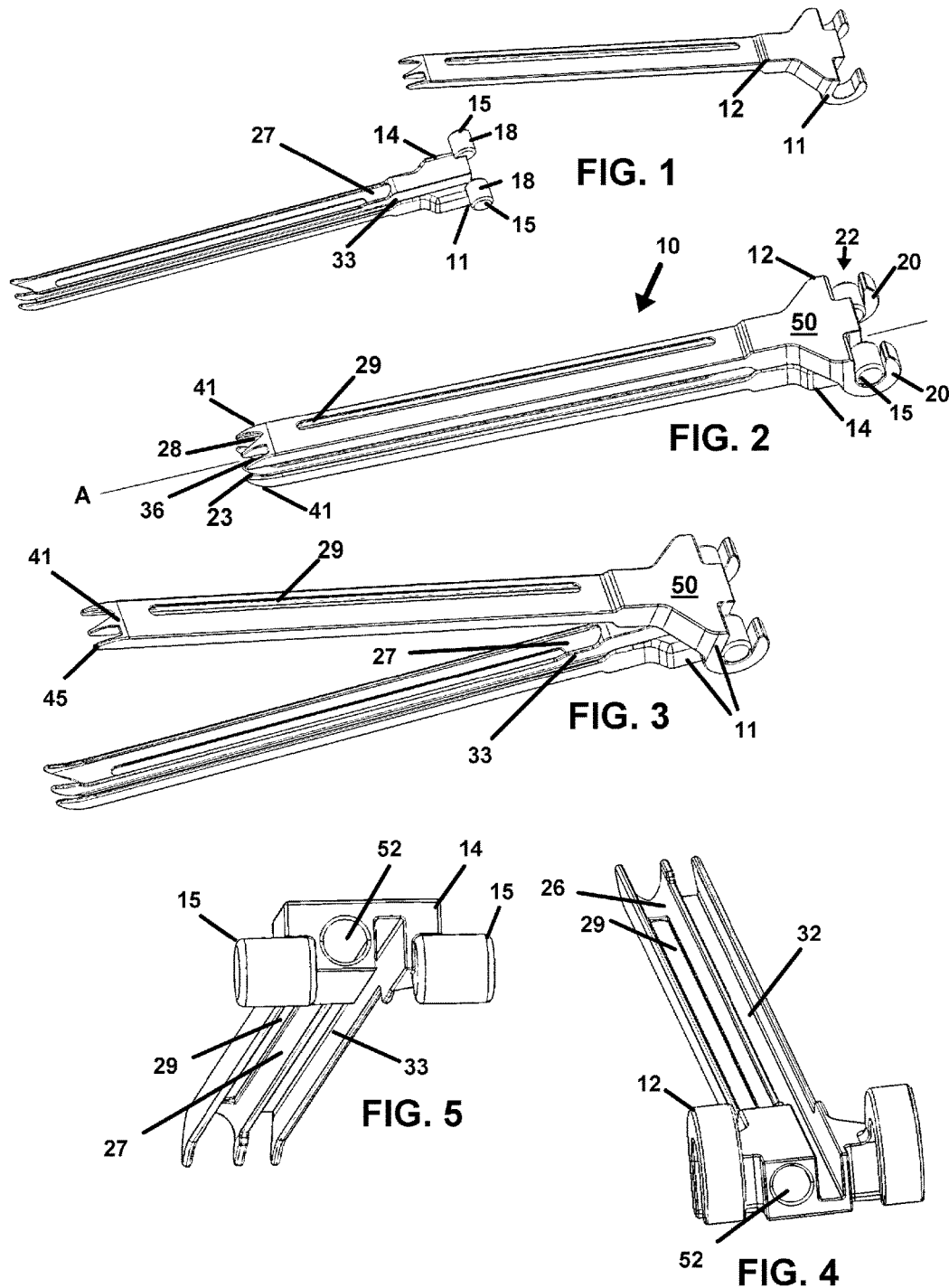

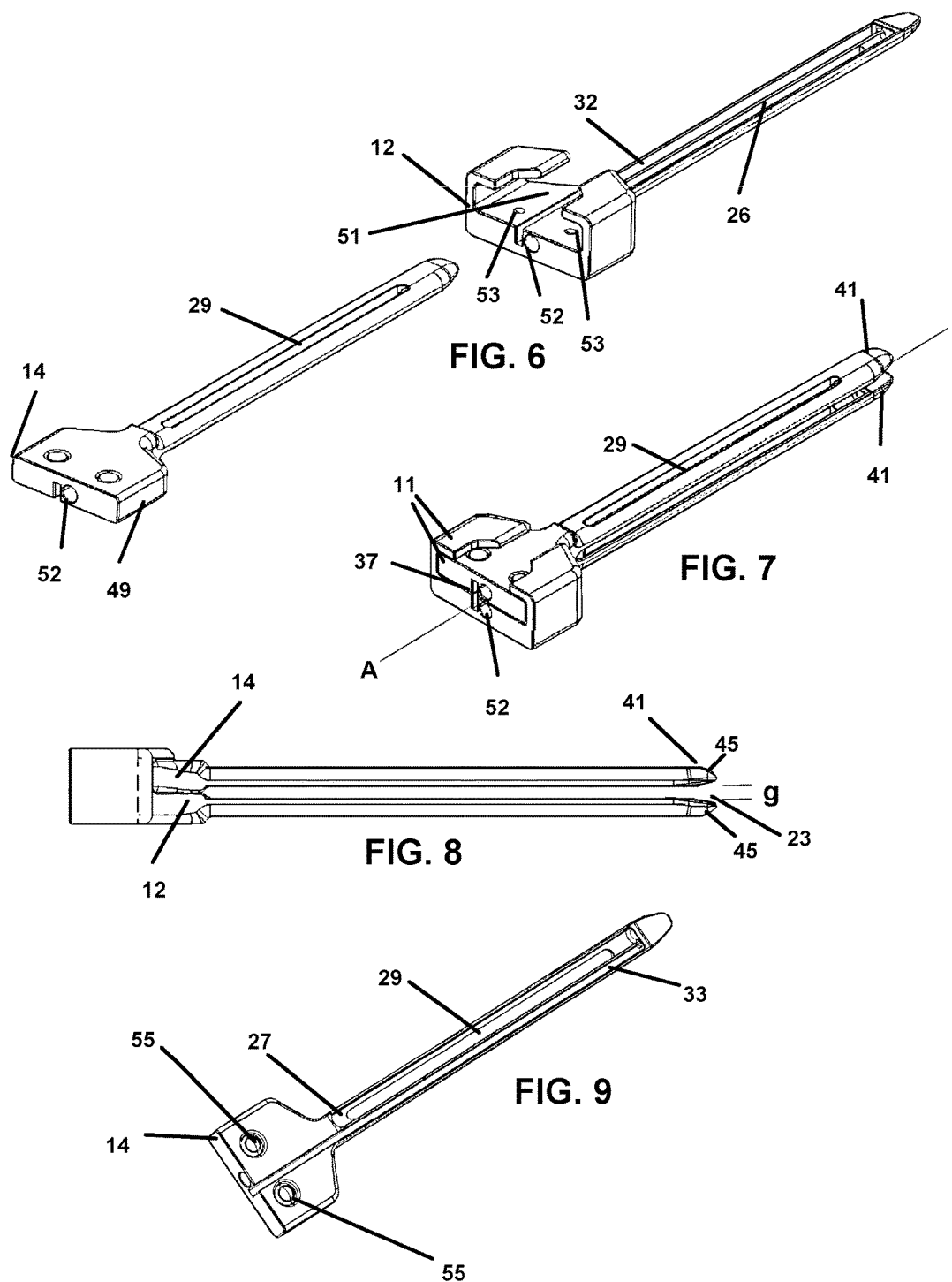

SURGICAL GUIDE

This application claims priority to U.S. Provisional Patent Application Ser. No. 61/909,907 filed on Nov. 27, 2013, and is inclusive thereof in its entirety by this reference hereto.

BACKGROUND OF THE INVENTION

1. Field of the Invention

The disclosed device concerns surgical instruments employed in minimally invasive surgery. More particularly, the disclosed device and method relate to an apparatus and method employable as a guide for a cooperatively configured blade, for cutting anatomic members, such as ligaments, during minimally invasive surgical procedures.

2. Prior Art

Many surgical procedures on patients, for correction of an injury or a problem brought about by disease, are performed using minimally invasive surgery where surgical implements are positioned within the patient's body and guided by the surgeon using a video depiction of the surgical site communicated over a fiber optic line. Such procedures generally require the surgeon to make incisions or cuts for removing, releasing, or relocating body tissue, for instance, surgery for ulnar nerve release in the cubital tunnel or for a carpal tunnel release (also known as carpal tunnel decompression surgery). In these and similar surgeries, the goal is to cut an adjacent ligament without damaging any proximate nerves, blood vessels, muscle or body tissue.

Such procedures generally include endoscopic or arthroscopic procedures for entering the patient and severing a ligament or other body tissue which is causing the patient harm or pain, with an anterograde knife, retrograde knife, or other blade as shown in U.S. Pat. No. 5,651,790. Herein lies a significant shortcoming in prior arts, as visibility for the surgeon performing this delicate procedure is minimal since it consists of a display on a video screen of the site which is captured by a small lens at the distal end of a fiber optic or other electronic transmission line.

The depicted surgical site is also shown in a somewhat unnatural orientation and under artificial light projected from the same or a coaxial fiberoptic line. However, concurrently, the need for surgical precision and the surgeon's confidence in their movement to make incisions and cut tissue with great accuracy is paramount.

Positioning of the blade or knife, which the surgeon will employ for severing the ligament or other tissue causing the problem, requires the employment of a guide. The guide is either inserted first to form a pathway for the knife to the site of the internal surgery, or inserted concurrently with the knife engaged within the guide. The guide provides a shield around the sharp portions of the blade during transition to the surgical site.

However, conventional guides only provide a channel forming the blade pathway, on a single surface of a single elongated planar member. This configuration generally requires that the blade have a width shorter than the adjacent sidewalls of the channel providing the pathway in the guide. However, the side of the blade which is not positioned adjacent to the surface of the channel, can contact body tissue when the blade is translated within the channel since the channel only has three sides. Thus, damage can be done to the patient during such translation.

Additionally, conventional planar guides with channels for a cabled imaging component and surgical blades or knives can only form a pathway through tissue the height of the sidewall of the guide. Body tissues, however, are quite pliable and incisions running though skin and fat layers tend to collapse and impede translation of the guide into position within the body of the patient. Further, during such translation the exposed side of the blade can cause incisions and other damage to body tissues since those tissues tend to bias or deform against the open channels formed in the guide.

As such, there is a continuing unmet need for an improved surgical guide device with formed pathways for both a surgical knife or blade, and for translation of optical cable of a cable imaging component employed for communicating the video depiction of the surgical site from the image capturing device. Such a device should provide the appropriate adjacent channels for the surgical blade and optical cabled imaging component in a manner which prevents tissue contact against the blade and the optical cable. Further, such a device should be employable by the user to widen or enlarge passages through which it needs to translate when needed. Still further, such a device should be capable of use with open channels when such are advantageous but reconfigurable to yield closed channels, or tunnels in the primary mode of use.

SUMMARY OF THE INVENTION

The device and method of employment herein disclosed and described achieves the abovementioned goals for a surgical knife or blade guide, and remedies the noted shortcomings of prior art through the provision of a significantly enhanced guide which configures two engageable members to form tunnels for both the blade or knife and the cabled imaging component running through the guide. Additionally provided are viewing apertures running through the tunnel formed for the optical cable or cabled imaging component allowing translation therethrough of the lens end to view tissue located on both sides of the sidewalls forming the tunnel.

Using a novel means for removable engagement of both members, the device employs a first member and a second member which are either slidably or rotationally engaged at respective proximal ends and which extend to respective distal ends. When placed in this adjacent position in this engagement, a first channel formed into the first member is in registered alignment with a first channel formed in the opposing second member to thereby form a first tunnel. This first tunnel is adapted to allow translation of a fiber optic or similar transmission cabled imaging component therethrough.

Additionally formed in the first tunnel, one or a plurality of apertures formed in the channel wall of the first member and/or second member provide viewing apertures to view adjacent tissue or body structures on both sides of the assembled device using the fiber optic component translating through the formed tunnel.

Also formed into the surface of the first member is a second channel which is in a registered opposing position with a second channel formed in the second member when the two members are in rotational engagement. This second channel provides a covered pathway with which the knife or blade may translate and thereby be prevented from contact with body tissues positioned on both sides of the engaged members.

A first means for engagement of the two members at proximal ends is provided by a particularly preferred means for rotational engagement of the first and second members at their respective proximal ends. Currently, this engagement is provided by an axle projecting from both sides of one of the two members which engages with a race formed on each of a pair of curved members extending from the other of the two members. However, other means for rotational engagement can be used and are anticipated within the scope of this patent.

A second preferred means for engagement of the two members at the proximal ends of each, is a sliding engagement where cooperative projections on one member slidably engage into complimentary slots on the other member. This is done using projections on one member sized and shaped to engage with a surrounding race on the other of the two members. This slidable engagement can yield a static attachment or rotational engagement depending on the shape of the sliding engagement. A sliding engagement of open ended hooked members on projecting axles will yield such a rotational engagement.

In this registered engagement of the opposing members, it is preferred that both are positioned substantially parallel to each other. Further, it is preferred that a small gap be maintained at the distal end of the engaged members to allow for viewing through the fiberoptic system through the end.

When in a rotational engagement, the two members provide opposing surfaces configured for compression between a thumb and opposing finger of the user such as a surgeon. Compression of the opposing contact surfaces results in an increase in separation distance of the two distal ends, and thus can be used to widen an incision or to push an adjacent ligament, blood vessel, or other body tissue away from the distal end of the assembled device.

It is an object of this invention to provide channels formed as tunnels in surgical guides for fiber optic cables and surgical blades or knives.

It is a further object of this invention to provide such a guide which is rotationally engaged at a proximal end to allow a separation at the distal end through compression of the proximal end.

It is a further object of this invention to provide the two opposing members forming the device in a separable fashion which allows their use without the other opposing member.

These together with other objects and advantages which become subsequently apparent reside in the details of the construction and operation of the disclosed surgical guide as more fully hereinafter described and claimed, reference being had to the accompanying drawings forming a part thereof, wherein like numerals refer to like parts throughout.

With respect to the above summary, before explaining at least one preferred embodiment of the herein disclosed ligament release surgical tool in detail, it is to be understood that the disclosed surgical guide invention is not limited in its application to the details of construction and to the arrangement of the components in the following description or illustrated in the drawings. The surgical guide herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other surgical guides and structures, and for other methods and systems for carrying out the several purposes of the present disclosed device. It is important, therefore, that the claims be regarded as including such equivalent construction and methodology insofar as they do not depart from the spirit and scope of the present invention.

BRIEF DESCRIPTION OF DRAWING FIGURES

FIG. 1 shows two engageable components of one preferred mode of the device in an exposed view.

FIG. 2 is an isometric perspective view of the surgical guide device in an engaged mode with the two opposing members of FIG. 1, in a registered engagement through a rotational engagement at respective proximal ends.

FIG. 3 depicts the device of FIG. 2, rotated to an open arrangement showing opposing channels in each half which combine when closed to define tunnels through the device to openings formed in the tapered distal ends.

FIG. 4 depicts an isometric proximal end view of one member showing an aperture leading to a fiber optic channel and a second channel for translation of a surgical blade therethrough which when in registered engagement forms tunnels.

FIG. 5 shows an isometric proximal end view of the opposing engageable member and showing the fiberoptic or video channel and second channel.

FIG. 6 depicts an exploded view of two engageable opposing members of another favored mode of the device herein.

FIG. 7 shows a removably engaged mode of the two members of FIG. 6, showing them in a slidable engagement fixing both halves in registered positions to each other.

FIG. 8 provides a side view of the device if FIG. 7, but also applicable to the device of FIG. 2, showing the gap formed between the engaged members.

FIG. 9 shows a first side surface of one member of the pair from FIG. 6 and showing the biased balls projecting and ready for engagement with detents shown in the other half in FIG. 6.

Figure 10:
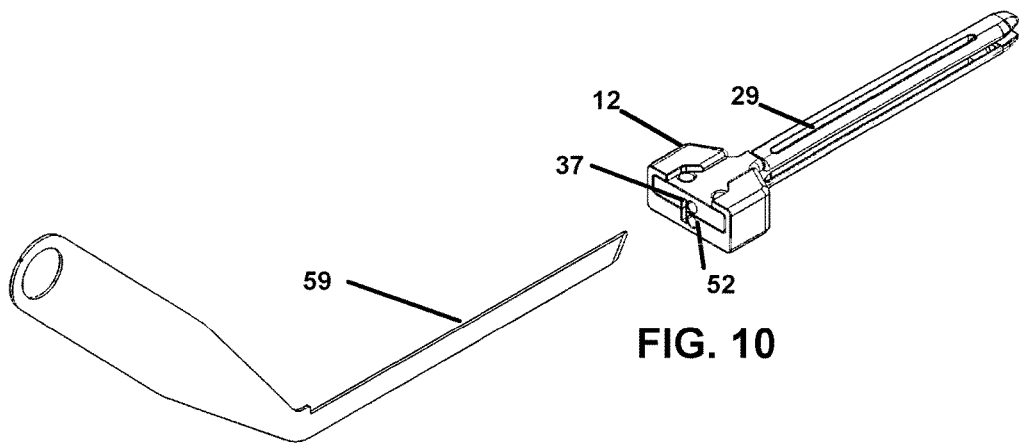

FIG. 10 shows the device of FIG. 7, as it would be positioned in the as-used position inserted within a patient and having a formed channel therein for translation of the blade.

Figure 11:
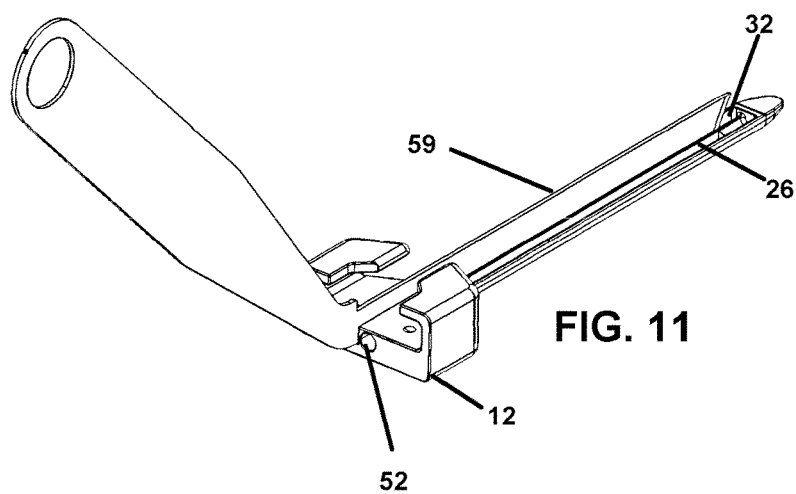

FIG. 11 depicts the blade of FIG. 10 inserted with one half removed from the assembly so as to provide a view of both the channel formed for the blade and for the fiber optic or electronic cabled imaging component.

Figure 12:
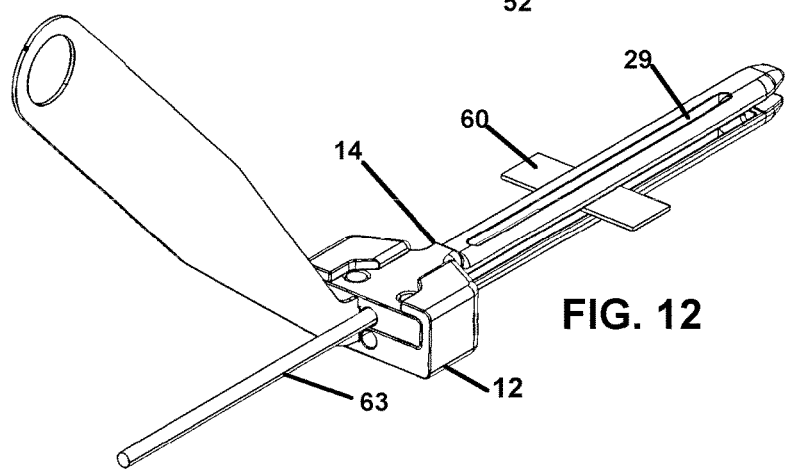

FIG. 12 shows the device as in FIG. 11 in an as-used position with tissue to be severed in a sandwiched position within the gap between the two members and both the blade and fiberoptic viewing component with camera or lens inserted in respective channels.

DETAILED DESCRIPTION OF THE PREFERRED EMBODIMENTS OF THE INVENTION

Referring now to the drawings in FIGS. 1-11, where the same components are identified with the same numeral, there is seen in FIG. 1, one mode of the device 10 in a disassembled configuration. A first member 12 and second member 14 are engageable at respective proximal ends 11 of each respective member of the pair, employing means for removable engagement of the proximal end of the first member with the proximal end of the second member 14 to maintain a registered positioning of each member, in receptive positions running parallel and with both aligned and running along a common axis.

In this assembled configuration, preferably running from adjacent the proximal end to the distal ends of the opposing members a gap 23 (FIG. 8) is maintained by contact point between the opposing two members at positions adjacent the proximal end, and a recessed edge of each member extending away from the contact point. This gap 23 is very important to all modes of the device 10 in that it provides a protected cutting space for a sandwiched engagement of tissue to be cut by the device 10 when engaged within the body of a patient.

The device 10 in all modes herein, achieves this assembled configuration, through a removable engagement at the respective proximal ends of each of the first member 12 and second member 12. One preferred means for registered removable engagement or a disengageable connection is shown in FIG. 2-3 wherein the first member 12 is a connection which is rotationally engaged with a curved race 18 extending in a curve around projecting members 15 extending from sides of the second member 14. This engagement of the curved race 18 having a diameter across facing portions of the curved race 18 slightly less than the diameter of the projecting members 15 maintains both members in a registered positioning with each other when closed as in FIG. 2, with both running along the same axis A, in removably fixed positions. It is this removable means for engagement of both respective side edges, of both members to each other, which maintains the members aligned with each other and with the axis A, during use in such removable engagement.

When the two members 12 and 14 are in the engaged configuration of FIGS. 2-3 and 7-8, by a connection therebetween at their respective proximal ends, they are in a registered engagement which is substantially fixed in the direction running along the axis A of both members such that they will not slide in a direction along the axis A while engaged, as well as deviate from this alignment laterally from the axis A. If the means for engagement or disengageable connection of the proximal ends is the rotational engagement as shown in FIGS. 1-5, the two members are fixed and not translatable along the axis 23, while in the engaged position separated by the gap 22, but easily separable by sliding the projecting curved race 18 through the gap 22 when the first member 12 with the curved members 20 has its long axis perpendicular to that of the second member 14. Means for removable registered engagement or the disengageable connection of opposing first member 12 and second member 14a which fixes the members from translating along the axis 23, could also be accomplished by a sliding engagement to a removably fixed positioning, such as shown in FIG. 6-8 and as discussed below.

As noted, the device 10 and method of employment when in the engaged mode of FIGS. 2 and 7, forms parallel tunnels for translation of a blade 59 or knife (FIGS. 10-12) in one, and translation of a cabled imaging component 63 or optical cable positionable in the other.

In both modes of the device 10 herein, employing the noted means for removable engagement of the proximal ends of the first member 12 and second member 14, and positioning of the members adjacent as in FIG. 1 or FIG. 7, a first channel 26 formed into the first member is in registered alignment with a first channel 27 formed in the opposing or second member 14 to thereby form a first tunnel having said gap 23 therebetween. This first tunnel 28 is adapted to allow translation of a cabled imaging component 63 such as a fiber optic imaging component with a fiber optic cable with lens or similar cabled imaging component 63 using a fiber optic or electronic cable engaged to a miniature camera or similar cabled imaging component providing a viewable image to the user.

In this first tunnel 28, one or a plurality of sequential apertures 29 may be formed in the channel wall of the first member 12 and/or of the second member 14. These viewing apertures 29 are preferred in all modes as they provide a window through the device 10 whereby the electronic or fiber optic viewing component can capture images therethrough of adjacent tissue or body structures on both sides of the assembled device 10. This allows the surgeon or other user to view and ascertain that body tissue which should not to be cut, is positioned outside the gap 23 between the two members and placed out of position for any cutting by the knife or blade 59.

Also formed into the surface of the first member 12 is a second channel 32 which is in a registered opposing position with a second channel 33 formed into a facing surface of the second member 14. When the two members are adjacent and engaged at their proximal ends the adjacent respective second channels form a second tunnel 36. This formed second tunnel defines a pathway adjacent the center axis A of the device 10 in which a knife or blade 59 may translate safely and not cut body tissue outside the gap. The second tunnel 36, within the gap 23 and separated from tissue outside the gap 23 thereby provides a pathway which separates the moving knife or blade 59, from contact with body tissues exterior to the gap 23.

In the engaged mode of FIGS. 1 and 7, where both members and both respective channels are in a registered opposing positioning, it is as noted, preferred that both the first member 12 and second member 14 are positioned with their long axis running substantially parallel to each other and the axis A.

Additionally preferred is such a parallel positioning of the two members in a removably fixed engagement to prevent translation, to form a gap 22 at the distal end 41 of both members having a width "g" maintained at the distal end 41 of the engaged members. Further, a curve 45 (FIG. 8) of the exposed distal surfaces of both members is preferred to provide an inward taper of the distal end 41 of the assembled engaged device 10. Openings 47 may be placed at the distal termination of the channels communicating through the tapered portion as shown in FIGS. 2-3.

When in the engaged position of FIG. 1, in the rotational means for engagement of FIGS. 2-3, the two members have opposing surfaces 50 positioned for a compression contact between a thumb and opposing finger of the user such as a surgeon. This compression of the opposing contact surfaces 50 results in a biased increase in separation distance of the two distal ends 41, and thus can be used as a means to widen an incision in a passage through the body, or to push an adjacent ligament, blood vessel, or other body tissue away from the distal end 41 of the assembled device 10.

FIG. 4 depicts a proximal end view of the device 10 in all modes depicting the first member 12 of the device 10 showing an access aperture 52 for communicating with the first tunnel 28, for translation of a cabled imaging component 63 and the second channel 32 forming half of the second tunnel 36 for translation of a blade 59 or knife therethrough as in FIG. 12.

FIG. 5 shows a typical view of the proximal end of the second member of the device 10 showing a second access aperture 52 for communicating the fiberoptic imaging device into the first tunnel 28 when the device is in the closed position shown in FIG. 2 or 7.

FIG. 6 depicts an exploded view of two engageable opposing members of another favored mode of the device herein.

Shown in FIG. 6 is an exploded view of the first member 12 and second member 14 in another preferred mode of the device 10 wherein a sliding engagement at the proximal ends of both members forms a removable engagement of the members. The second member 14 has a proximal end 49 shaped in a complimentary fashion to a recess 51 formed at the proximal end of the first member 12. Detents 53, are positioned in positions within the recess 51 to engage with biased projections 55 on a mating surface of the second member 55 and the proximal end 49 thereof. When the second member 14 is engaged as in FIG. 7, with the first member 12, the projections 55 slide into a removable engagement with the detents 53. This engagement maintains both the first member 12 and second member 14 in a fixed positioning running along the axis A. The projections can be spring loaded to retract and project from the second member 14 such that force must be exerted in opposite directions to the first member 12 and second member 14 to separate them from an engagement as in FIG. 7. Conversely, the spring loaded or biased projections 55 will when engaged in the detents 53 will maintain the fixed positioning of the first member 12 to the second member 14 along the axis A, and prevent translation along the axis A by either when in the engaged position of FIG. 7.

FIG. 7 as noted shows the device 10 in the engaged position where the first member 12 and second member 14 are held in fixed positions to each other and prevented from translation relative to each other along the axis A. As noted the members are held in this engaged positioning as long as the projections 55 are engaged in the detents 53 or other means for engagement of the proximal ends of the members will do the same.

As noted, FIG. 8 provides a side view of the device 10 such as in FIG. 7, but also applicable to the device of FIG. 2. Shown is the gap 23 extending in between the engaged first member 12 and second member 14.

FIG. 9 shows a first side surface of the second member 14 of the pair from FIG. 6-7. As can be seen, the biased projections 55 are positioned and extending from the surface at the proximal end of the second member and ready for engagement with the detents 53 in the first member 12 when slid into the engagement shown in FIG. 7. Disengagement is possible by simply employing sufficient force in opposite directions to each of the two members along the axis A until the projections translate into a recess housing them temporarily and dismount from the detents 53. Of course re-engagement would be in the reverse.

FIG. 10 shows the device of FIG. 7, as it would be positioned in as-used position inserted within an incision through the skin of a patient. In the as-used position, the proximal ends of the engaged members are left exposed, while all or a portion of the parallel first and second members extend into the body of the patient. Shown also are the two access apertures 52 providing access through the proximal ends for the fiber optic cabled or electronic cable of a cabled imaging component 63 to translate into the first tunnel 28 during use to provide a video display of the tunnel 28 and surrounding body tissue through viewing through the viewing apertures 29 communicating between the first tunnel 28 and surrounding tissue.

Additionally seen in FIG. 10 is the opening 37 communicating through the proximal ends and into the second tunnel 33 for translation of the blade 59 into the engaged device 10 for cutting tissue 60, such as a tendon for instance, which has been positioned in the gap 23 as shown in FIG. 12. As noted above, the opening 37 is formed by positioning the two members in the engaged position of FIG. 2 or 7, wherein the second channel 32 formed in the first member is adjacent and aligned with the second channel 33 formed into a facing surface of the second member 14.

FIG. 11 depicts the blade 59 of FIG. 10 inserted into the device of FIG. 10, except with the second member 14, removed from the assembly so as to provide a view of the second channel formed into the first blade 12, providing a protected pathway for translation of the blade 59 to cut only tissue 60 positioned within the gap 22.

FIG. 12 shows the device as in FIG. 10 in an as-used position with tissue 60 being severed where it has been positioned in a sandwiched position within the gap 22 between the two members. Also shown is the fiberoptic or electronic cable for the cabled imaging component 63 communicating through one of the access apertures 52 and into the first tunnel 28 having the viewing apertures 29.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed is:

1. A surgical device, comprising:
   a first member extending from a proximal end to a distal end and having a first surface opposite a second surface;
   a first channel defined by a first channel wall descending into said first surface and extending in-between said distal end and proximal end of said first member;
   a second channel defined by a second channel wall descending into said first surface running in-between said distal end and said proximal end, said second channel formed adjacent said first channel;
   a first side edge at said proximal end communicating between said first surface and said second surface;
   a first aperture communicating through said first side edge with said first channel, said aperture sized to accommodate translation of a cabled imaging component therethrough;
   at least one viewing aperture communicating through said first channel wall and through said second surface for providing a view of tissue surrounding said surgical device to said cabled imaging component;
   said second channel communicating through said side edge;
   whereby with said surgical device upon an insertion into the body of a patient through an incision to an as-used positioning, said cabled imaging component is translatable through said first aperture into said first channel for communicating images of areas surrounding said surgical device therefrom, and a blade for cutting chosen said tissue is insertable along said second channel forming a guided translational pathway for said blade;

a second member extending from a proximal end to a distal end and having a first surface opposite a second surface;

a first channel defined by a first channel wall descending into said first surface of said second member, and extending in-between said distal end and proximal end of said second member;

a second channel defined by a second channel wall descending into said first surface of said second member and extending in-between said distal end and said proximal end of said second member, said second channel formed in said second member formed adjacent said first channel thereof;

a second side edge at said proximal end of said second member communication between said first surface and said second surface thereof;

a second aperture communicating through said second side edge to said first channel of said second member, said second aperture sized to accommodate translation of said cabled imaging component therethrough;

said second channel formed in said second member communicating through said second side edge;

a disengageable cooperating connector engaging said first member and second member to form an assembled instrument, with respective first sides of each of said first member and said second member facing each other across a gap therebetween, said gap extending through opposing distal ends of said first and second members;

said first channel of said first member in position directly across said gap from said first channel of said second member defining a first tunnel of said assembled instrument;

said second channel of said second member in position directly across said gap from said second channel of said first member defining a second tunnel of said assembled instrument;

said second tunnel communicating through said second side edge and forming an opening for translation of said blade to said second tunnel;

said second aperture and said first aperture both providing individual separate pathways for said cabled imaging component to said first tunnel; and said gag positionable around said chosen tissue to be severed by said blade, whereby only said chosen tissue within said gap is severable and tissue surrounding said second tunnel with said surgical device in said as-used positioning is protected from such severing.

2. The surgical device of claim 1 additionally comprising:
said second surface at said distal end having a curved portion, said curve extending from a position on said second surface adjacent said distal end, to said distal end, said curve providing a path through said incision for reducing a force required for said insertion.

3. The surgical device of claim 1 additionally comprising:
a stop positioned in said second channel, said stop preventing translation of said blade past said distal end of said first member.

* * * * *

UNITED STATES PATENT AND TRADEMARK OFFICE
CERTIFICATE OF CORRECTION

Page 1 of 1

PATENT NO. : 10,245,062 B2
APPLICATION NO. : 15/106500
DATED : April 2, 2019
INVENTOR(S) : Stuart Seymour It is certified that error appears in the above-identified patent and that said Letters Patent is hereby corrected as shown below:

On the Title Page

Item (60), Provisional Priority Data, add "App No. 61/909,907 filed on November 27, 2013".

In the Specification

Column 5, Line 16 (approx.), change "FIG." to --FIGS.--.

Column 5, Line 51, change "FIG." to --FIGS.--.

Column 7, Line 41, change "FIG." to --FIGS.--.

In the Claims

Column 9, Line 15 (approx.), in Claim 1, change "communication" to --communicating--.

Column 10, Line 14 (approx.), in Claim 1, change "gag" to --gap--.

Signed and Sealed this
Twenty-eighth Day of April, 2020

Andrei Iancu
*Director of the United States Patent and Trademark Office*